US008173071B2

(12) United States Patent
Natarajan et al.

(10) Patent No.: US 8,173,071 B2
(45) Date of Patent: May 8, 2012

(54) MICRO-FLUIDIC TEST APPARATUS AND METHOD

(75) Inventors: Govindarajan Natarajan, Poughkeepsie, NY (US); Emmanuel Delamarche, Thalwil (CH); Eric A Eckberg, Rochester, MN (US); James N Humenik, LaGrangeville, NY (US); Kathleen A McGroddy-Goetz, New Fairfield, CT (US); Scott Partington, Raleigh, NC (US); Christopher F Perrera, Colchester, VT (US); Marco G Trivella, Raleigh, NC (US); Timothy M Wiwel, Raleigh, NC (US)

(73) Assignee: International Business Machines Corporation, Armonk, NY (US)

( * ) Notice: Subject to any disclaimer, the term of this patent is extended or adjusted under 35 U.S.C. 154(b) by 1180 days.

(21) Appl. No.: 11/468,091

(22) Filed: Aug. 29, 2006

(65) Prior Publication Data
US 2008/0057570 A1    Mar. 6, 2008

(51) Int. Cl.
*C12M 1/34* (2006.01)
(52) U.S. Cl. .............. 422/82.01; 422/82.02; 422/82.03; 422/68.1; 422/502; 422/500; 422/501; 422/507; 73/1.01; 73/1.02; 435/288.5; 435/287.2; 435/287.1; 435/91.2
(58) Field of Classification Search .............. 422/82.01, 422/68.1, 100, 501, 502, 503, 504, 505, 82.02; 73/64.47; 435/6, 91.2, 287.2
See application file for complete search history.

(56) References Cited

U.S. PATENT DOCUMENTS

| 4,269,197 | A |   | 5/1981 | Gilbard |
| 4,996,993 | A | * | 3/1991 | York ............................ 600/547 |
| 5,143,080 | A |   | 9/1992 | York |
| 6,437,551 | B1 | * | 8/2002 | Krulevitch et al. .......... 324/71.1 |
| 6,911,132 | B2 | * | 6/2005 | Pamula et al. ................ 204/600 |
| 6,919,046 | B2 | * | 7/2005 | O'Connor et al. ............ 422/100 |
| 7,017,394 | B2 | * | 3/2006 | Sullivan ....................... 73/64.47 |
| 7,129,717 | B2 | * | 10/2006 | Donsky ......................... 324/692 |
| 7,238,323 | B2 | * | 7/2007 | Knapp et al. ................. 422/68.1 |
| 7,338,637 | B2 | * | 3/2008 | Pease et al. ................... 422/100 |
| 7,670,559 | B2 | * | 3/2010 | Chien et al. ................... 422/100 |
| 7,674,545 | B2 | * | 3/2010 | Chun et al. .................... 422/100 |
| 2002/0100714 | A1 | * | 8/2002 | Staats ............................ 422/100 |
| 2002/0127736 | A1 | * | 9/2002 | Chou et al. .................... 422/100 |
| 2002/0174937 | A1 |   | 11/2002 | Burdon et al. |
| 2003/0129646 | A1 | * | 7/2003 | Briscoe et al. .................... 435/6 |

(Continued)

FOREIGN PATENT DOCUMENTS

CN          1603818 A       4/2005
(Continued)

OTHER PUBLICATIONS

SIPO Office Action dated Apr. 8, 2011.
(Continued)

*Primary Examiner* — In Suk Bullock
*Assistant Examiner* — Sharon Pregler
(74) *Attorney, Agent, or Firm* — Joseph Petrokaitis; Roberts Mlotkowski Safran & Cole, P.C.

(57) ABSTRACT

An apparatus, system, and method for determining the osmolarity of a fluid. The apparatus includes at least one micro-fluidic circuit and at least one electrical circuit disposed in communication with the at least one micro-fluidic circuit for determining a property of a fluid contained within the at least one micro-fluidic circuit.

15 Claims, 13 Drawing Sheets

U.S. PATENT DOCUMENTS

| | | | |
|---|---|---|---|
| 2004/0036485 A1* | 2/2004 | Sullivan | 324/694 |
| 2004/0043479 A1* | 3/2004 | Briscoe et al. | 435/288.5 |
| 2004/0147032 A1* | 7/2004 | Martin et al. | 436/69 |
| 2004/0238052 A1* | 12/2004 | Karp et al. | 137/822 |
| 2005/0104606 A1* | 5/2005 | Donsky | 324/692 |
| 2005/0120772 A1 | 6/2005 | Sullivan et al. | |
| 2005/0201895 A1 | 9/2005 | Donsky | |
| 2006/0083661 A1* | 4/2006 | Chun et al. | 422/100 |
| 2006/0194331 A1* | 8/2006 | Pamula et al. | 422/100 |

FOREIGN PATENT DOCUMENTS

| | | |
|---|---|---|
| CN | 1675532 A | 9/2005 |
| WO | WO 2005026665 A2 * | 3/2005 |
| WO | 2005/076796 A2 | 8/2005 |
| WO | 2005/089207 A2 | 9/2005 |

OTHER PUBLICATIONS

SIPO Office Action dated Aug. 24, 2011.

* cited by examiner

MICRO-FLUIDIC TEST APPARATUS AND METHOD

FIELD OF THE INVENTION

The invention generally relates to an apparatus, system, and method for measuring the osmolarity of a relatively small volume of fluid, and more particularly to an apparatus, system, and method for measuring the osmolarity of human tears.

BACKGROUND OF THE INVENTION

Dry eye syndrome (DES), also known as keratoconjunctivitis sicca (KCS), is a condition that occurs due to loss of water from the tear film and is one of the most common complaints seen by optometrists. Studies have found that DES is common in about 15% of patients over the age of 50, with prevalence increasing with age. Dry eye in general is caused by any condition that increases tear film evaporation or by any condition that decreases tear production. For example, evaporation may be increased as a result of having larger eyes (i.e., having more surface area for evaporation to occur from). Also, tear production may decrease from any condition that decreases corneal sensation, such as long term contact lens wear, laser eye surgery, trauma to the $5^{th}$ nerve, and certain viral infections, etc.

The treatment of DES depends on the severity of the condition. Some patients find relief through the use of various artificial tears. Others utilize supplements containing Omega-3. Still others resort to the insertion of punctual plugs to stop the drainage of tears. Effective treatment, however, begins with effective diagnosis.

In order to diagnose DES, it is useful to determine the osmolarity of the tears in the affected eye. Osmolarity is the measure of the concentration of osmotically active species in a solution, and may be quantitatively expressed in osmoles of solute per liter of solution. It is known that when the tear film loses water, salt and protein concentrations increase relative to the amount of water, resulting in increased osmolarity. Therefore, in order to diagnose and treat DES patients, it is desirable for a treating physician to quantify the osmolarity of a sample tear fluid.

Current techniques for measuring osmolarity involve osmotic pressure measurement, freezing point depression analysis, vapor pressure measurement, and electrical resistance measurement. In one approach, an osmometer is used to measure the osmotic pressure exerted by a solution across a semi-permeable membrane. The osmotic pressure can be correlated to the osmolarity of the solution.

In another approach, the osmolarity of a sample fluid may be determined by an ex vivo technique that involves analyzing the freezing point of the sample fluid. Deviation of the sample fluid freezing point from 0° Celsius is proportional to the solute level in the sample fluid, and is indicative of the osmolarity.

In a further known ex vivo technique, a piece of filter paper is placed under the patient's eyelid to absorb tear fluid. The paper is removed and placed in an apparatus that measures a dew point. The reduction in dew point proportional to that of water can be converted to an osmolarity value.

Lastly, osmolarity may be determined by measuring the conductivity of a fluid sample. The measurement may be made in vivo by placing electrodes under the eyelid. Alternatively, the measurement may be made ex vivo by collecting a sample from the patient and transferring it to a measurement apparatus.

Known techniques for measuring osmolarity, such as those described above, rarely produce accurate or consistent results because they suffer from problems including, for example, inducement of reflex tearing and evaporation of fluid samples. Reflex tearing occurs when the tear glands of the patient are stimulated during tear collection. The stimulation produces extra amounts of liquid, which can lead to false readings (e.g., too high water content). Conversely, when very small samples are taken to avoid reflex tearing, the small samples often immediately begin to evaporate, which can lead to false readings (e.g., too low water content).

Accordingly, there exists a need in the art to overcome the deficiencies and limitations described hereinabove.

SUMMARY OF THE INVENTION

In a first aspect of the invention, an apparatus comprises at least one micro-fluidic circuit and at least one electrical circuit disposed in communication with the at least one micro-fluidic circuit for determining a property of a fluid contained within the at least one micro-fluidic circuit.

In a second aspect of the invention, a system for measuring osmolarity of a fluid comprises a carrier comprising a through hole, a gripper, a mover, and an expeller. The through hole is structured and arranged to be aligned with a test site. The gripper is structured and arranged to grip a collector. The mover is structured and arranged to align the collector with the through hole.

In a third aspect of the invention, a method for determining osmolarity of a fluid comprises receiving into a gripper a collector having a fluid sample and moving the collector into alignment with a test site. The method further comprises expelling the fluid sample from the collector into the test site, measuring a property of the fluid sample within the test site, and displaying a value of the property.

DETAILED DESCRIPTION OF EMBODIMENTS OF THE INVENTION

The invention is directed to a system and method for determining the osmolarity of fluids, such as, for example, human tears. According to the invention, the osmolarity of a fluid can be determined in a clinically feasible manner, on a nanoliter scale, and with the capability for reduced evaporation, by measuring at least one electrical property (e.g., resistance, conductivity, etc.) of the fluid. In this manner, implementations of the invention may be used for providing accurate and consistent osmolarity measurements, thereby facilitating the diagnosis and treatment of pathological conditions.

Figure 1:
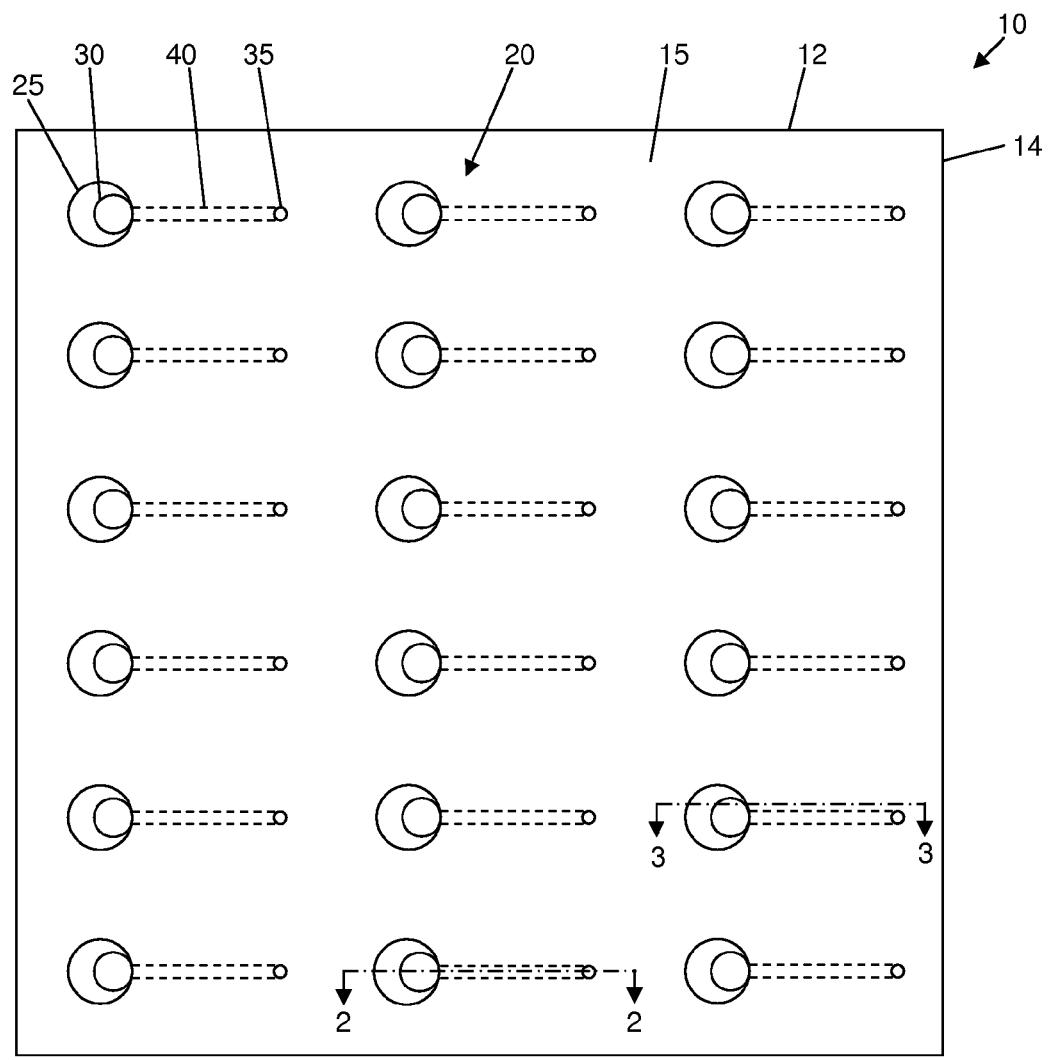
FIG. 1 shows top view of a test chip according to aspects of the invention.

FIG. 1 shows a chip 10, according to implementations of the invention. The chip 10 is provided with at least one test site that can be used for determining at least one electrical property (e.g., resistance, conductivity) of a fluid. The osmolarity of the fluid may be determined from a predetermined correlation to the determined electrical property.

In embodiments, chip 10 has a first side edge 12, second side edge 14, and first surface 15 on which is located at least one test site 20. Although the chip 10 is shown as rectangular, it is understood that the chip 10 may have any shape (e.g., oval, circular, etc.) In embodiments, the chip 10 has eighteen test sites 20, although other numbers of test sites are contemplated by the invention. The test site(s) 20 may be arranged in any suitable pattern (e.g., rectangular grid, radially, etc.) on the chip 10. Each test site comprises a first hole (e.g., large hole 25) and a vent hole 35. Moreover, each test site 20 further comprises a second hole comprising a first portion (e.g., small hole 30) having a diameter smaller than the first hole, and a connecting tunnel (shown as 40). The large hole 25, small hole 30, tunnel 40, and vent hole 35 combine to form a micro-fluidic circuit, described in greater detail below. Although the invention is described in terms of a micro-fluidic circuit, it is understood that the invention may be implemented in any suitable scale (e.g., micro-fluidic, nano-fluidic, etc.). In embodiments, individual or multiple chips 10 may be packaged in a protective vacuum-sealed bag.

Figure 2:
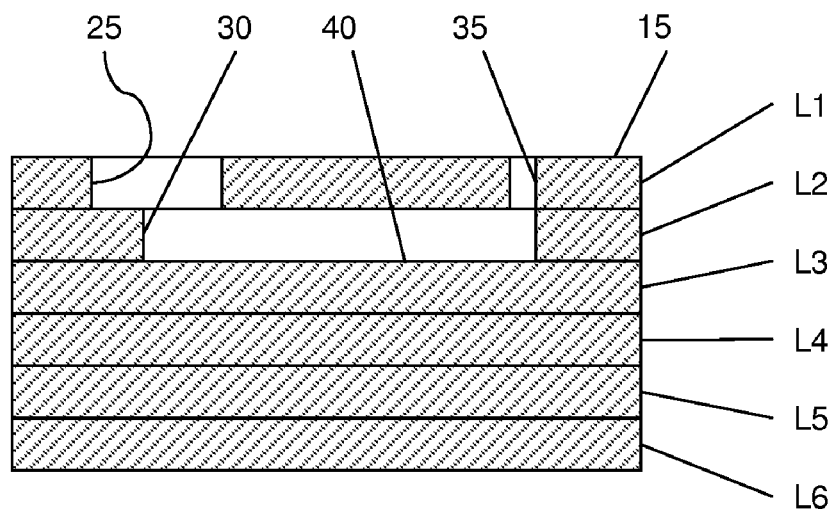
FIG. 2 shows sectional view taken along line 2-2 of FIG. 1.

The chip 10 may be composed of any suitable material. In embodiments, the chip 10 is composed of a layered structure (for example, a ceramic laminate structure formed by stacking and sintering multiple personalized layers). For example, as shown in FIG. 2, the chip 10 may comprise six layers (L1, L2, L3, L4, L5, L6) of glass ceramic material, each layer being composed of a mixture of silica, alumina, magnesia, and binder (e.g., organic binder). Each layer may have a thickness of about 2 mils to 6 mils.

In embodiments, each layer and its associated features are separately formed and then assembled to create the chip 10. For example, a hole having a diameter of about 1100 microns is formed in the first layer L1 to create the large hole 25. The large hole 25 may be formed in any suitable manner, such as, for example, cutting, laser drilling, water knife, sand blasting, overlap punching, etc. Similarly, a hole having a diameter of about 300 microns is formed in the first layer L1 to create the vent hole 35. A hole having a diameter of about 500 microns is formed in the second layer L2 to create the small hole 30. And a hole connected to and extending from the small hole 30 and having a width of about 100 microns and a length of about 3500 microns is formed in the second layer L2 to create the tunnel 40. It is noted that other suitable dimensions may be employed. The layers are stacked such that the large hole 25 overlaps the small hole 30, and the vent hole 35 overlaps an end of the tunnel 40. In this way, an enclosed (e.g., buried) micro-fluidic circuit is formed that is less susceptible to the effects of evaporation.

When a fluid sample (e.g., a tear) is deposited in the large hole 25, the fluid will flow into the offset small hole 30 by way of gravity. The fluid will flow from the small hole 30 into the tunnel 40, toward the vent hole 35, by capillary action. The rate at which the fluid flows through the tunnel 40 can be estimated from the rate of capillary action (e.g., from the dimensions of the micro-fluidic circuit and the properties of the fluid) and the rate of evaporation of the fluid. The time from depositing the fluid into the large hole 25 to the fluid reaching any location in the tunnel 40 may be estimated with the rate and known dimensions of the micro-fluidic circuit.

Figure 3:
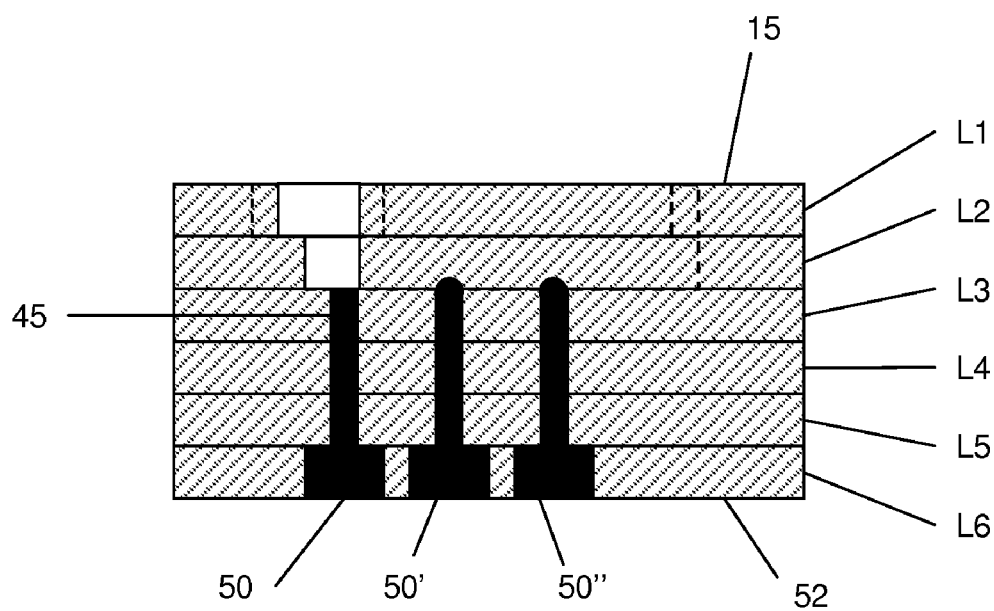
FIG. 3 shows sectional view taken along line 3-3 of FIG. 1.

In addition to the micro-fluidic circuit, each test site 20 includes at least one electrical circuit for measuring at least one electrical property (e.g., resistance) of the fluid contained in the micro-fluidic circuit. In embodiments, the electrical circuit comprises lines of electrically conductive material deposited in holes formed through layers L3, L4, L5, and L6, as shown in FIG. 3. For example, vias 45 are formed in substantially identical locations in layers L3, L4, and L5. Larger pads 50 are formed in corresponding holes in bottom layer L6.

Figure 4:
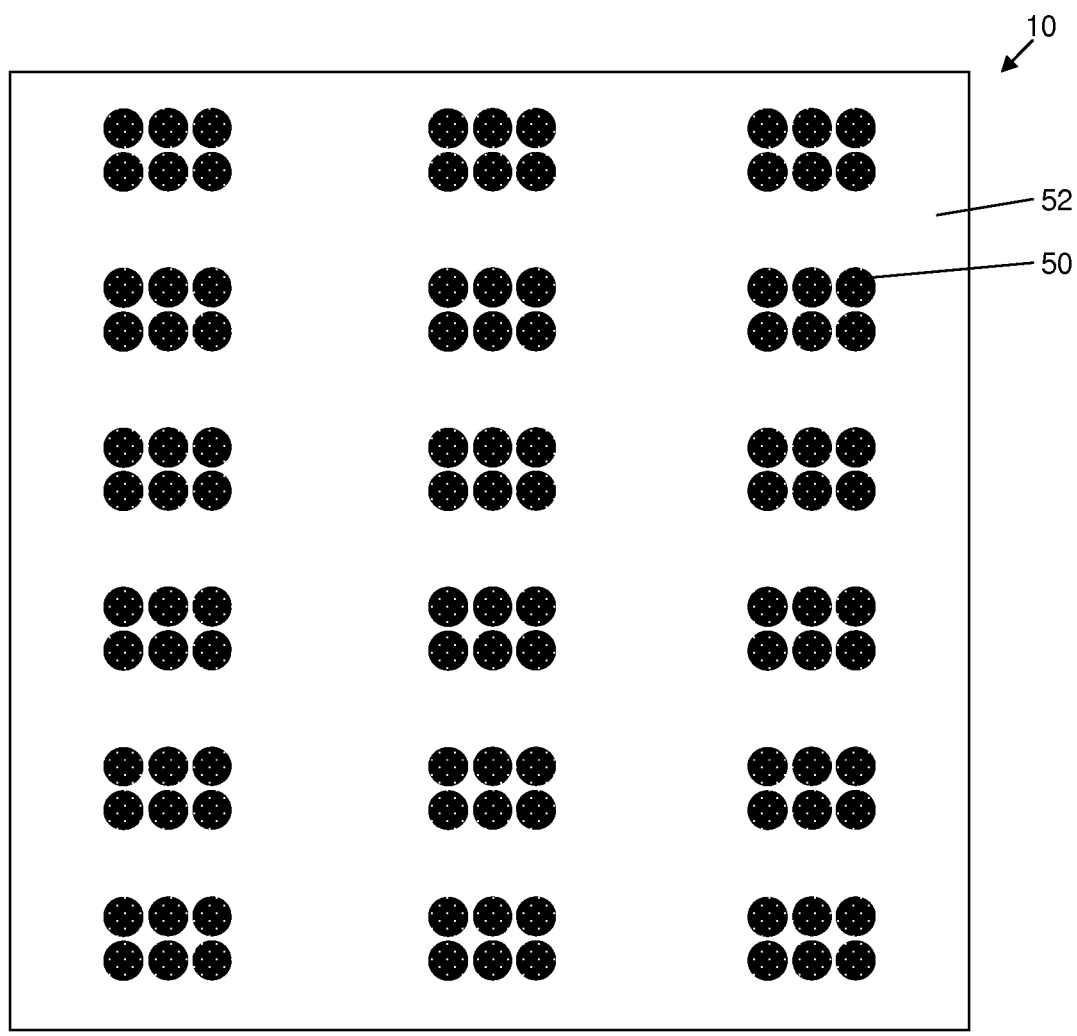
FIG. 4 shows bottom view of the test chip according to aspects of the invention.

The pads 50 are exposed on the bottom surface 52 of the chip 10, as shown in FIG. 4, such that measuring equipment may be electrically connected thereto. Each via 45 and pad 50 may comprise, for example, a hole formed in the respective layer and filled with an electrically conductive material. The electrically conductive material may be any suitable material, such as, for example, gold, silver, copper, nickel, platinum, etc., and composites thereof. In embodiments, the electrically conductive material comprises a metal paste that is composed of a mixture having about 56% copper, 14% nickel, and 30% glass (e.g., glass ceramic) by volume. This composition is resistant to oxidation in storage and use, and has a very low resistance relative to that of intended sample fluids.

Figure 5:
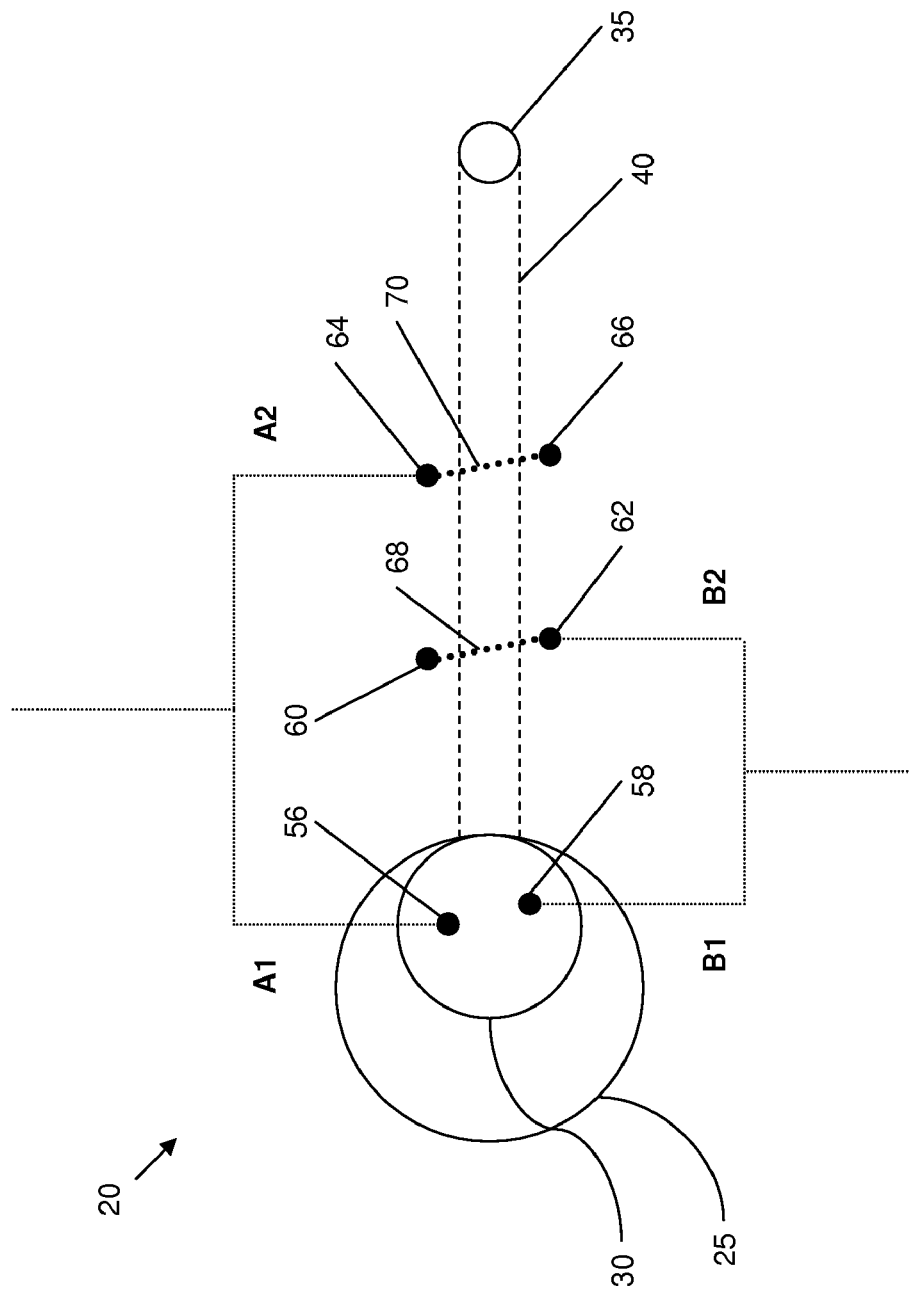
FIG. 5 shows a schematic representation of a circuit according to aspects of the invention.

In the exemplary implementation shown in FIG. 5, six different vias 56, 58, 60, 62, 64, and 66 are shown as part of the electrical circuit for a test site 20. Two vias 56 and 58 are disposed within the perimeter of the small hole 30. Two vias 60 and 62 are formed on either side of the tunnel 40 at a first downstream location along the tunnel 40. Two vias 64 and 66 are formed on either side of the tunnel 40 at a second downstream location along the tunnel 40. Additionally, a first electrode 68 extends across the tunnel 40 connecting vias 60 and 62, and a second electrode 70 extends across the tunnel 40 connecting vias 64 and 66. In embodiments, the first and second electrodes are formed by depositing an electrically conductive material on the surface of third layer L3. For example, the same metal paste as used in the vias may be printed onto the third layer using known techniques.

Still referring to FIG. 5, the two electrodes 68, 70 traverse the tunnel 40 at locations downstream from the small hole 30. The respective vias are electrically connected as schematically shown by dotted lines. When a fluid fills the small hole 30, the fluid will create an electrical connection between the vias 56 and 58. The resistance of the fluid between the circuit elements A1:B1 may be measured in a known manner, as described in greater detail below. Moreover, the time of the measurement may be noted, such as, for example, by starting a timer. As the fluid moves through the tunnel 40 by capillary action, it will cross first electrode 68. At this point, the resistance of the fluid between the circuit elements B2:B1 may be measured. As the fluid continues to move through the tunnel 40, it will cross second electrode 70, at which point the resistance between circuit elements A2:A1 may be measured. Similarly, a measurement may be made between the first electrode 68 and second electrode 70.

In embodiments, the above-described features may be varied to achieve desired effects on the fluid sample. For example, the diameter of the vent hole and the diameter of the cross-section of the tunnel may be kept small to reduce the area of the air-liquid interface so as to reduce evaporation of liquid from the fluid sample. Furthermore, the separation distances between the small hole and the first electrode, or between the venting hole and the second electrode can be made large to increase the time needed for diffusion of species toward the electrodes. Even further, the tunnel may be formed in a non-linear path (e.g., curved, zigzag, meandering, etc.) to increase the distances for diffusion without making the footprint of the micro-fluidic circuit substantially larger.

Figure 6:
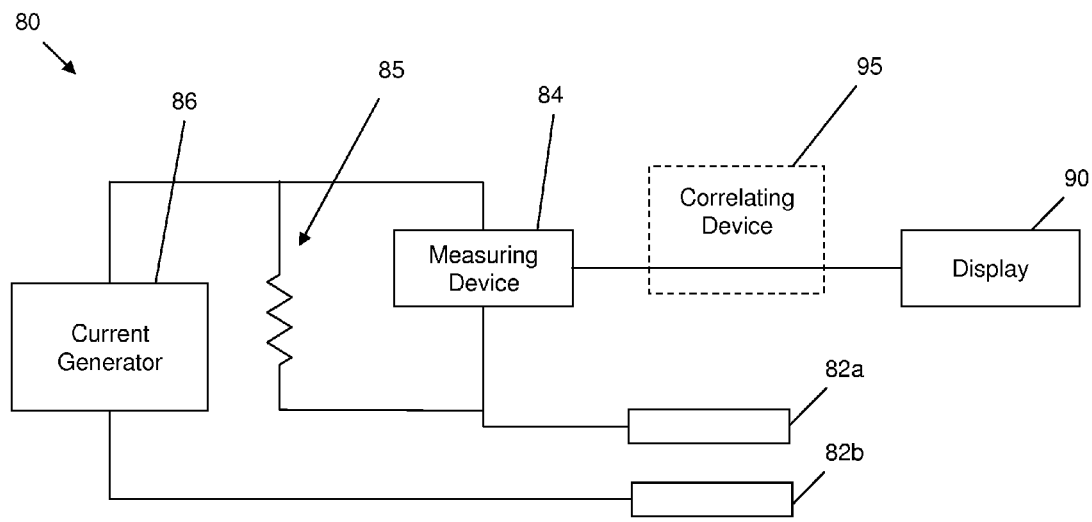
FIG. 6 shows a schematic representation of a determiner according to aspects of the invention.

FIG. 6 schematically shows a determiner 80 for determining the osmolarity of a fluid sample held in the micro-fluidic circuit of a test site. In embodiments, electrically conductive probes 82a, 82b are connected to two respective pads (50' and 50") of a chip. For example, a first probe 82a (e.g., pogo probe, alligator clip, etc.) may be laid upon, clipped to, or slidingly brought into contact with a first pad that is connected to a first via 60, and a second probe 82b may similarly be brought into contact with an other pad that is connected to an other via 64. In embodiments, the probes 82a, 82b are also connected to a measuring device 84, bridge 85, and current generator 86. For example, the measuring device 84 may comprise an rms voltmeter, the bridge 85 may comprise a 100 Kohm resistor, and the current generator 86 may comprise a signal generator. When a fluid sample is placed in the large hole 25 and fills the small hole 30, the fluid will close a circuit between vias 60, 64. A current, such as, for example, a 100 kHz sinusoidal signal from the generator 86, can be applied to the circuit, and at least one electrical property (e.g., resistance) of the fluid may be determined, as will be understood by those of skill in the art. Certain electrical properties (e.g., conductivity, resistance) of the fluid are directly related to the ion concentration of the fluid in a known manner. Because the ion concentration is related to the osmolarity of the fluid, the osmolarity may be determined from the at least one measured electrical property.

Similar measurements can be made when the fluid closes the circuit between first electrode 68 and via 58, and when the fluid closes the circuit between second electrode 70 and via 56. Although two electrodes are depicted, any number of electrodes may be used at any locations throughout the micro-fluidic circuit. In this manner, numerous measurements of the same property of the fluid may be made and compared, thereby increasing the reliability that the measurements are accurate. For example, a routine statistical analysis may be performed on the numerous measurements to determine a confidence factor that can then be compared to a pre-determined pass/fail threshold.

In embodiments, the determiner 80 comprises a display 90 that displays the measured value from the measuring device 84. For example, the display 90 may comprise an LCD display that displays a numerical value that corresponds to the measured electrical property of the fluid. A user may utilize a reference chart, based upon known correlation between the measured electrical property and the osmolarity, to convert the displayed numerical value to an osmolarity value. Optionally, a correlating device 95 that automatically correlates the measured electrical property to the osmolarity may be disposed between the measuring device 84 and the display 90. The correlating device 95 may comprise, for example, a computer processor that receives the value of the measured electrical property, converts the value of the measured electrical property to an osmolarity value by accessing look-up tables or correlation equations, and outputs the osmolarity value to the display 90.

Figure 7:
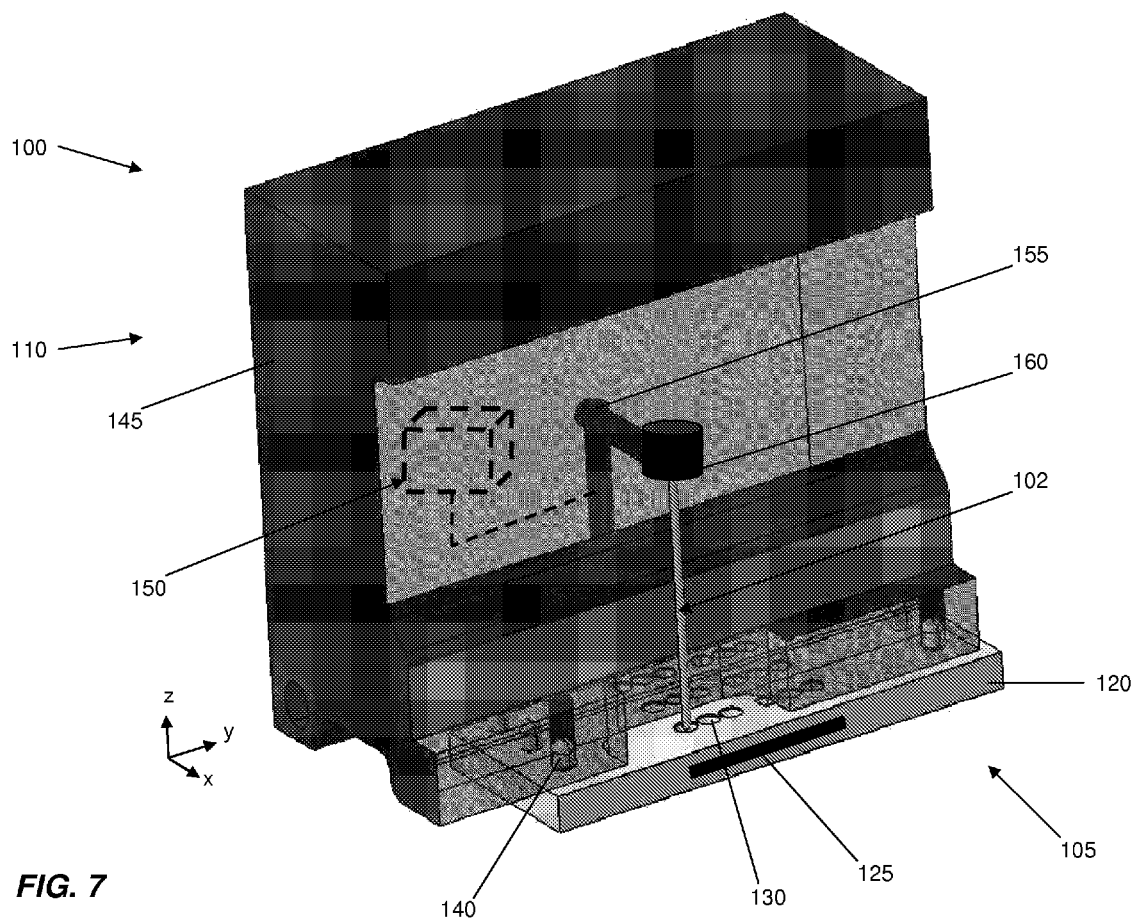
FIG. 7 shows a system according to aspects of the invention.

FIG. 7 shows a system 100 according to aspects of the invention. In embodiments, the system 100 comprises a collector 102, carrier 105, and test stand 110. The system 100 may also include a chip 10 as described above. In this manner, the system may be used to determine the osmolarity of a fluid.

In embodiments, the collector 102 comprises a micropipette or a capillary tube, and is used for collecting the fluid sample to be tested. For example, a micropipette can be used to collect a tear from the human eye by way of capillary action and without inducing reflex tearing, as is known in the art. In embodiments, the collector 102 is sized to correspond to other elements of the system, as described below. For example, an outside diameter of an end of the collector 102 may be sized smaller than a diameter of the large hole but larger than a diameter of the small hole of a test site.

The carrier 105 includes a holding structure 120 for holding and aligning a chip. The holding structure 120 may be shaped and sized in any suitable manner, and may be composed of any suitable material. In embodiments, the holding structure 120 comprises a plate-like member that is formed of plastic, such as, for example, by injection molding. The holding structure 120 includes a receiving portion 125 that receives the chip. In implementations, the receiving portion 125 may be a slot disposed within the holding structure 120, and the chip may be slidingly received into the slot.

The holding structure 120 also includes funnels 130 that are arranged to be disposed above the respective test sites of a chip that is held in the receiving portion 125. For example, there may be eighteen funnels 130 that align with portions (e.g., the large holes) of the eighteen test sites of a chip that is held in the receiving portion 125. The funnels 130 facilitate precise placement of fluid samples onto the respective test sites (e.g., into the large holes).

In embodiments, the carrier 105 further comprises alignment devices, such as, for example, pegs 140 disposed on the top surface of the holding structure 120. The pegs 140 may be integral with or separable from the holding structure 120. The pegs 140 facilitate alignment of the carrier 105, and therefore the test sites of a chip held therein, with the test stand 110.

Still referring to FIG. 7, the test stand 110 includes a housing 145, a mover 150 adapted to move the collector 102, an expeller 155 adapted to expel a fluid sample from the collector 102, and a gripper 160 adapted to grip the collector 102.

The housing 145 is adapted to be removably connected to the carrier 105 via the pegs 140. In this manner, the test sites located on the chip within the carrier 105 may be precisely aligned with the other elements of the housing 145. The housing 145 may be of any suitable size and shape, and may be constructed of any suitable material.

The mover 150 is adapted to align a gripped collector 102 with a respective funnel 130 of the carrier 105. In embodiments, the mover 150 comprises any combination of one or more actuators (e.g., screw, rack and pinion, pneumatic, etc) that is arranged to move the collector 102 back and forth along three orthogonal axes (e.g., x, y, and z, as shown in FIG. 7). The mover 150 may also comprise one or more controllers (such as, for example, a programmable logic controller, microprocessor, etc.) for controlling the actuator(s). Such actuators and controllers are known in the art and may be housed separately from or within the housing 145. With knowledge of the dimensions of the housing 145, carrier 105, and collector 102, the mover 150 may be used to move the collector 102 into precise alignment with a respective funnel 130. Once aligned with a funnel 130, the mover 150 may cause the collector 102 to move through the funnel 130 to a position aligned with, and just above, a respective test site. In this manner, a fluid sample may be precisely aligned with a test site before the fluid sample is expelled from the collector 102 onto the chip.

The expeller 155 is adapted to expel the fluid sample from the collector 102 and onto the chip. In embodiments, this is accomplished by increasing the air pressure behind the fluid sample held in the collector 102. This may be accomplished in any known manner, such as, for example, using an elastic bulb, air pump, air compressor, etc. The increased air pressure pushes the sample out of the collector 102. When the collector 102 is aligned with the test site, as described above, the sample is expelled onto the test site (e.g., into the microfluidic circuit). The expeller, or components thereof, may be located inside or outside the housing 145.

Figure 8:
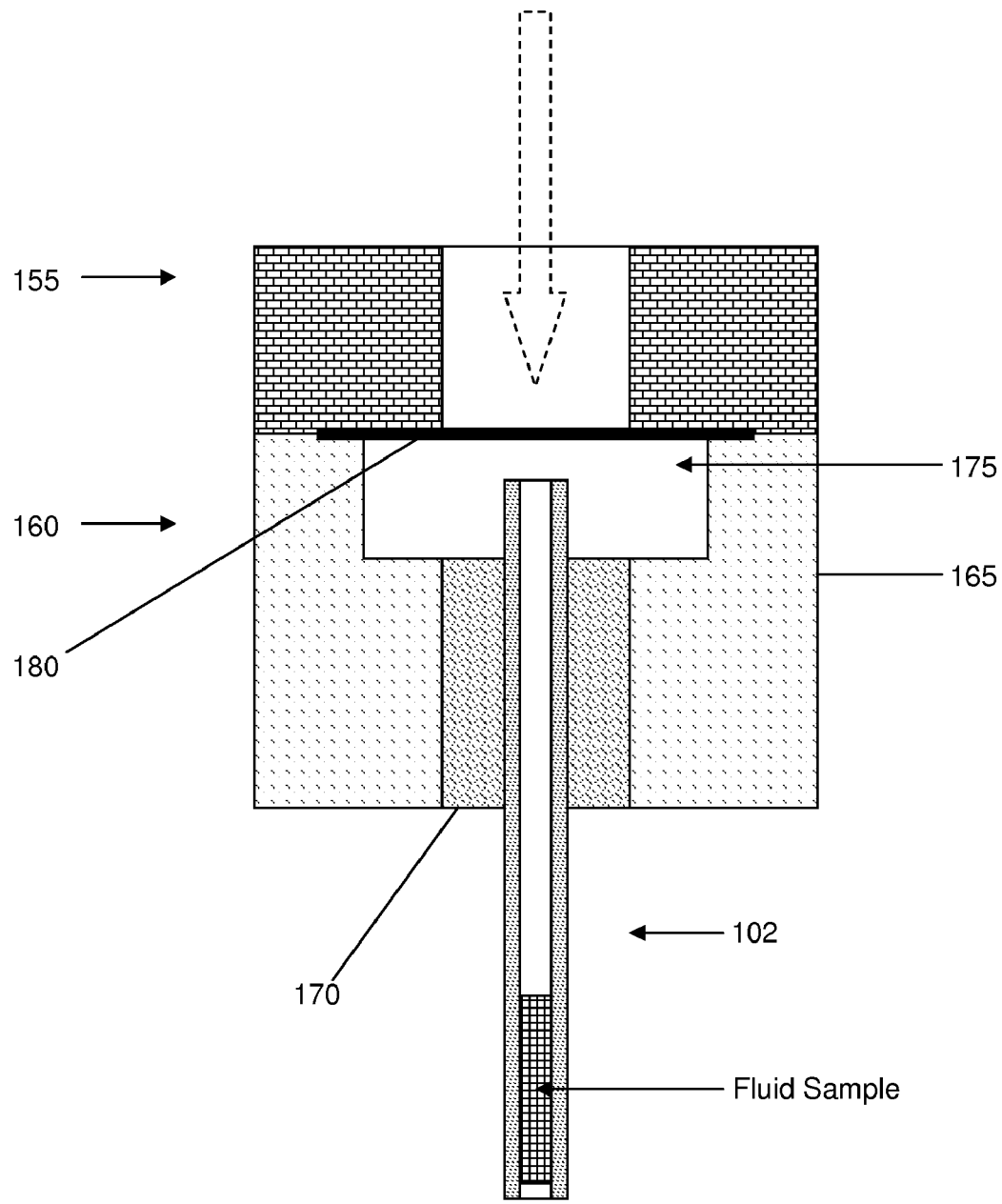
FIG. 8 shows a combined gripper and expeller according to aspects of the invention.

The gripper 160 is adapted to receive and hold the collector 102 such that the collector may be appropriately moved and the fluid sample expelled, as described above. In embodiments, the expeller 155 and gripper 160 are combined, as shown in FIG. 8. In this implementation, the gripper 160 comprises a gripper body 165 that hinges open and closed about an axis that is offset from and parallel to the longitudinal axis of the collector 102. When the gripper body 165 is hinged open, the collector 102 may be received in a seal portion 170. When the gripper body 165 is hinged closed around the collector 102 (as shown in FIG. 8), the seal portion 170 is arranged to grip the collector 102 without damaging it, and to provide a substantially airtight seal around the collector 102. Moreover, when the gripper body 165 is closed around the collector 102, the top end of the collector 102 is disposed within a gap 175.

Still referring to the implementation shown in FIG. 8, the expeller 155 comprises an elastically deformable membrane 180 that forms part of the boundary of the gap. In embodiments, the membrane 180 is composed of an elastomeric material, although any suitable material may be used. The expeller 155 also comprises any suitable device (e.g., piezoelectric actuator, air pump, etc.) for applying a force to the membrane 180 that will move the membrane 180 into the gap (as shown by the arrow in FIG. 8). Movement of the membrane 180 into the gap increases the pressure behind the fluid sample in the collector 102, such that the fluid sample will be expelled from the collector 102.

Figure 9:
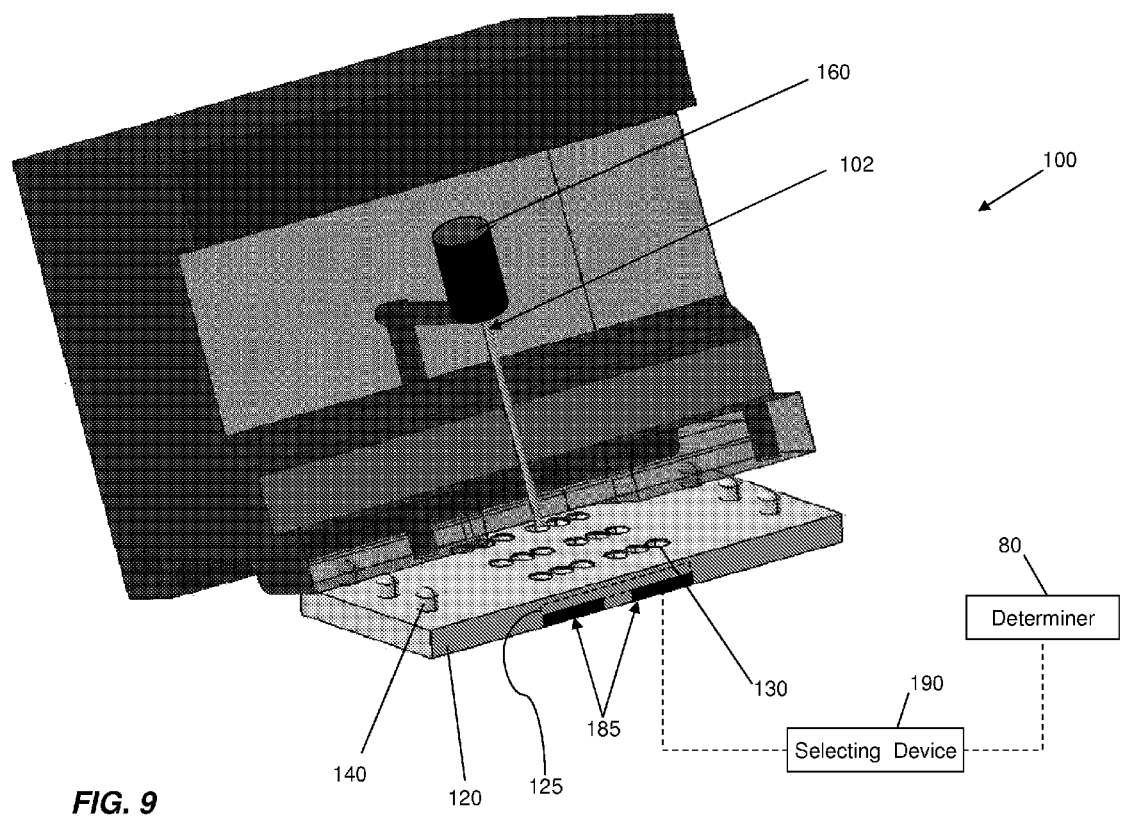
FIG. 9 shows a system according to aspects of the invention.

Further aspects of the system 100 are shown in FIG. 9. In embodiments, the holding structure 120 may comprise electrical contact portions 185 that are structured and arranged to come into contact with respective pads of a chip that is disposed in the receiving portion 125 of the carrier 105. The electrical contact portions 185 may be connected to a measuring device, as will be apparent to the skilled artisan, such that the osmolarity of the fluid in a particular test site may be determined. For example, for a chip having eighteen test sites and six pads per test site, the holding structure 120 may be provided with one hundred and eight (i.e., six times eighteen) individual contact portions 185. In this manner, every single pad of the chip will be in contact with a respective contact portion 185 of the carrier when the chip is received in the receiving structure 125.

In embodiments, the contact portions 185 are further connected to a determiner 80, such as that described above, for determining the osmolarity of the fluid(s) in the test site(s). For example, the contact portions 185 may be connected (e.g., wired) to a selecting device 190 (e.g., switch, processor, microprocessor, etc.) that is, in turn, connected to the probes of the determiner 80. As will be understood by the skilled artisan, the selecting device 190 can be operated to isolate any two respective contact portions 185, such that the resistance of the fluid that completes the circuit between the pads that are in contact with the two respective contact portions 185 can be determined with the determiner 80. In this manner, the osmolarity of the fluid that completes the circuit between the pads can be determined.

The selecting device 190 and/or determiner 80 may be housed separately from the other elements of the system 100, such as, for example, in a handheld device or desktop computer. Alternatively, the selecting device 190 and/or determiner 80 may be integrated into the carrier 105 or test stand 110. Additionally, an input device (e.g., keypad, buttons, switches, etc.) for providing input to the various controllers of the system may be housed separate from or integrated with the carrier 105 or test stand 110.

Figure 10A:
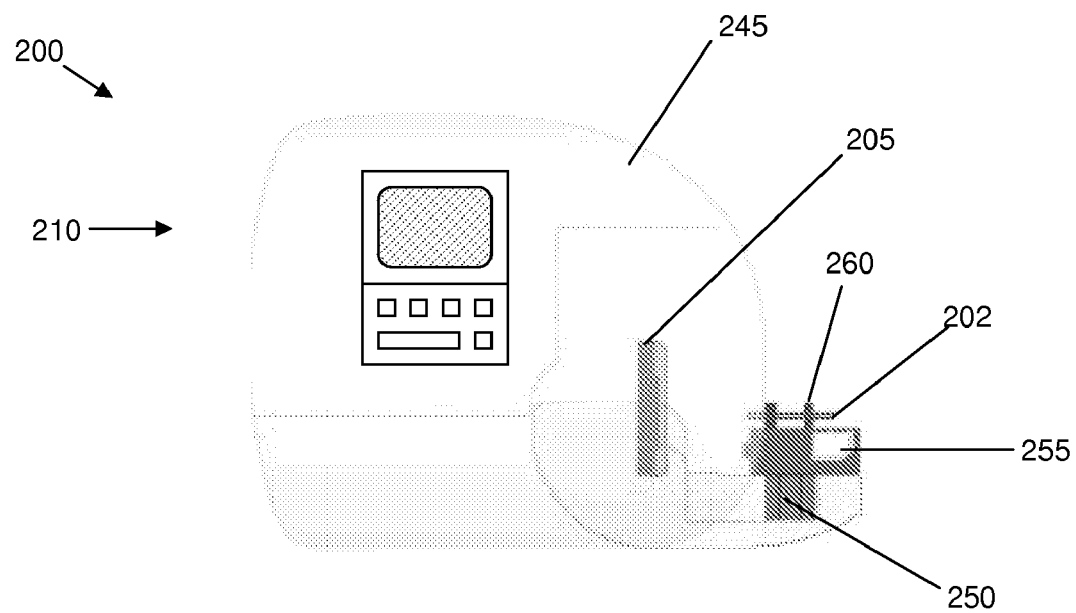
FIGS. 10A and 10B show another system according to aspects of the invention.
Figure 10B:
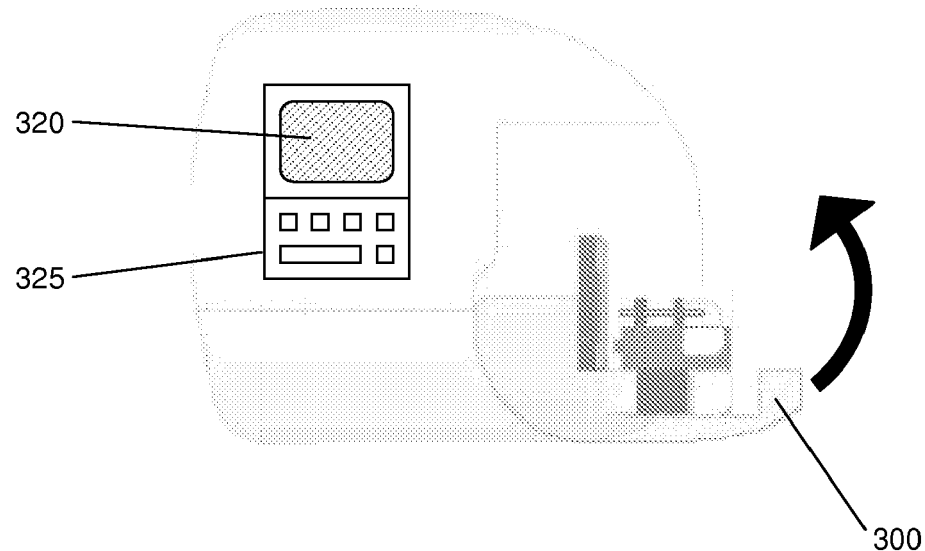

FIGS. 10A and 10B show an alternative system 200 according to aspects of the invention. In this embodiment, the system comprises a collector 202, carrier 205, and test stand 210. The collector 202 and carrier 205 may be similar to those described above. In embodiments, the test stand 210 includes a housing 245, mover 250, expeller 255, and gripper 260, which may be similar to those described above.

In this implementation, the test stand 210 also comprises a hinged door 300 attached to the housing 245, as shown in FIG. 10B. The hinged door 300 may carry portions of the carrier 205, mover 250, expeller 255, and gripper 260. The door 300 may be opened for insertion of a chip, carrier 205, and collector 202 (with fluid sample) into the test stand 210. When the door 300 is closed, the system 200, via actuators and controllers, moves the collector 202 to the appropriate funnel of the carrier 205 and expels the fluid sample onto a test site. The movement and expelling may be automatic upon closing the door 300, or may require user input (e.g., from buttons, keypad, switch, etc.).

The system 200 (as well as the system 100 described above) may include an output display 320 (e.g., LCD, computer screen, etc.) for displaying information, such as, for example, the values determined by the determiner, menus and/or instructions for a user, etc. Additionally, the system 200 (as well as the system 100) may include an input device 325 (e.g., buttons, keypad, switch, etc.) for receiving input from a user. The display 320, input device 325, and a determiner (as described above) may be integrated into the housing 245.

Method of Use

FIGS. 11-14 are flow diagrams implementing steps of the invention. FIGS. 11-14 may equally represent a high-level block diagram of the invention. Some of the steps of FIGS. 11-14 may be implemented and executed from either a server, in a client server relationship, or they may run on a user workstation with operative information conveyed to the user workstation to create the navigation outlined above. Additionally, aspects of the invention can take the form of an entirely hardware embodiment, an entirely software embodiment or an embodiment containing both hardware and software elements.

In an embodiment, aspects of the invention are implemented in software, which includes but is not limited to firmware, resident software, microcode, etc. Furthermore, aspects of the invention can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W) and DVD.

Figure 11:
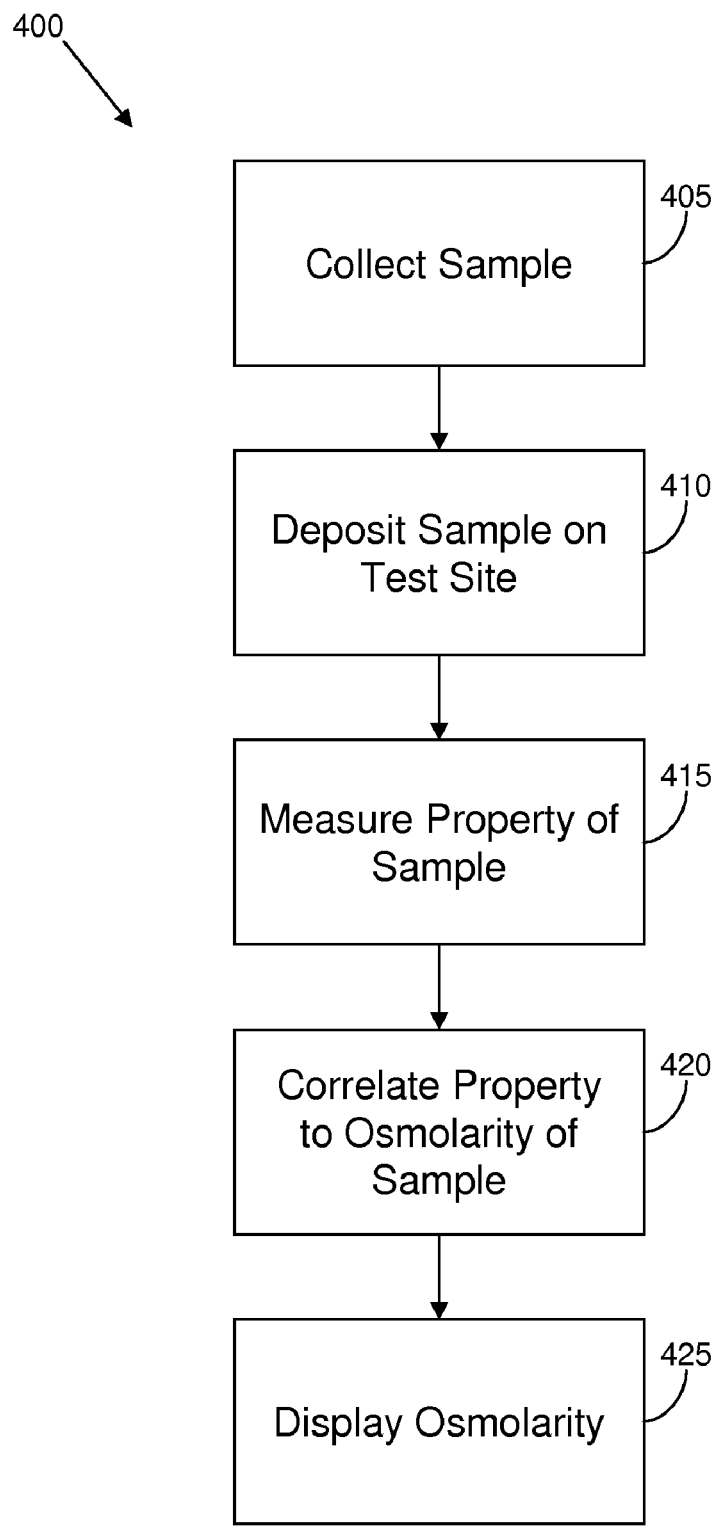
FIGS. 11-14 show flow diagrams depicting methods according to aspects of the invention.

FIG. 11 shows a first method 400 according to a first aspect of the invention. At step 405, a sample of fluid is collected for the purpose of determining the osmolarity of the fluid. In embodiments, the sample is collected with a collector, such as, for example, a micropipette or capillary tube, as described above. Such a collector may be used to draw fluid (e.g., tear, blood, etc.) from a patient (e.g., human, dog, cat, etc.), as should be apparent to those skilled in the art.

At step 410, the sample is deposited onto a test site. In embodiments, this comprises using one of the previously described systems 100, 200 to deposit the sample onto a test site of a chip such that the sample enters the micro-fluidic circuit. For example, a collector may be aligned with a portion of a test site (e.g., the large hole of the test site), and the sample expelled from the collector by increasing the air pressure behind the sample such that the sample is expelled onto the test site.

At step 415, at least one electrical property of the fluid is measured. In embodiments, this is accomplished using the determiner described above as the sample moves through the micro-fluidic circuit by capillary action. For example, a current may be applied to the appropriate electrical circuit, and the resistance (or conductance) of the fluid may be measured in a known manner.

At step 420, the measured value of the at least one electrical property of the fluid is correlated to an osmolarity value of the fluid. In embodiments, this is accomplished using a microprocessor that applies a look-up table or correlation equation to the value of the measured electrical property. Then, at step 425, the osmolarity value is displayed. In embodiments, the value is displayed on an LCD, computer screen, or similar display.

Figure 12:
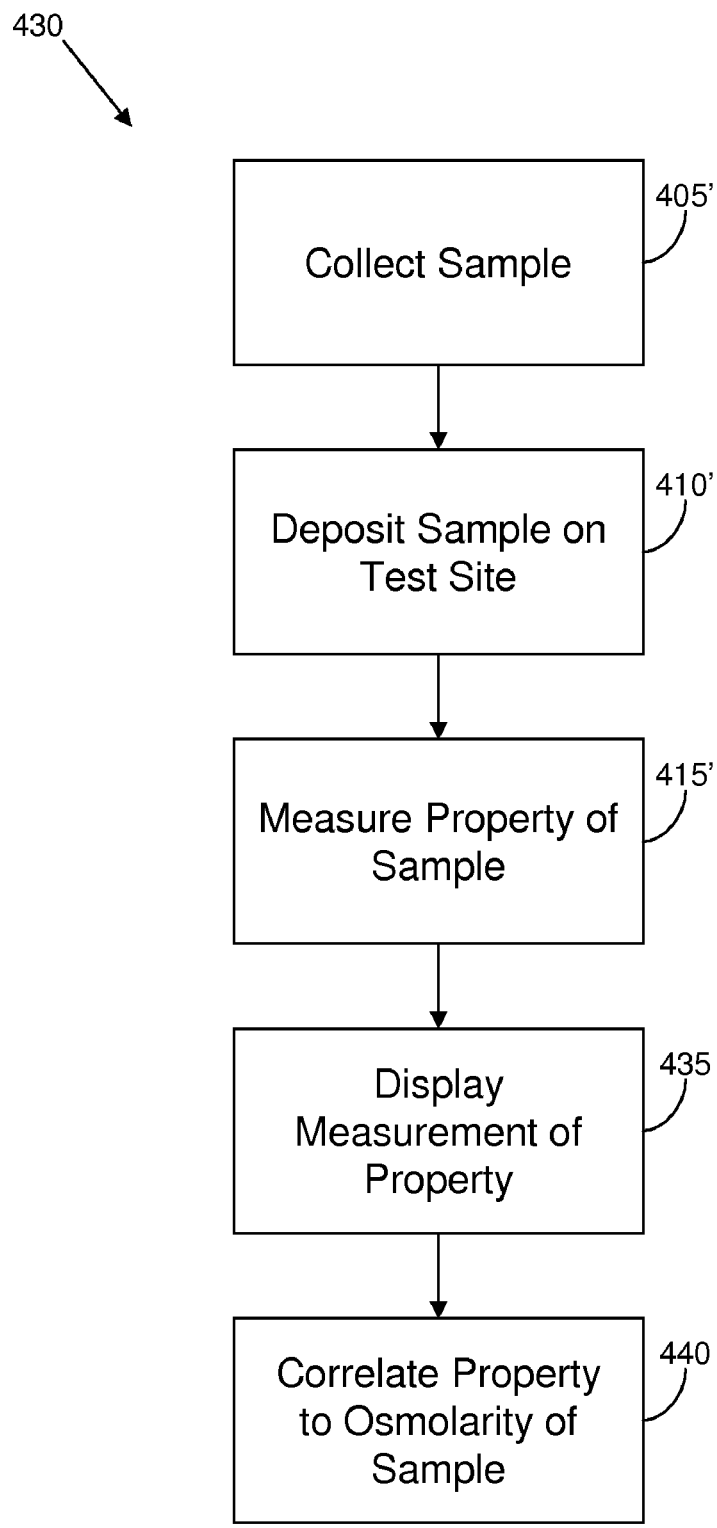

FIG. 12 shows a second method 430 according to a second aspect of the invention. The steps 405', 410', and 415' may be performed in a manner similar to steps 405, 410, and 415 of first method 400. However, in the second method 430, the value of the measured property is displayed at step 435 before correlating it to the osmolarity at step 440. For example, the value of the measured property, such as, for example, a voltage that corresponds to the measured property, is displayed at step 435. Then, at step 440, a user manually correlates the value to an osmolarity value by, for example, referring to a written chart. In this way, the second method 430 may be implemented without using an automatic correlating device (e.g., microprocessor).

Figure 13:
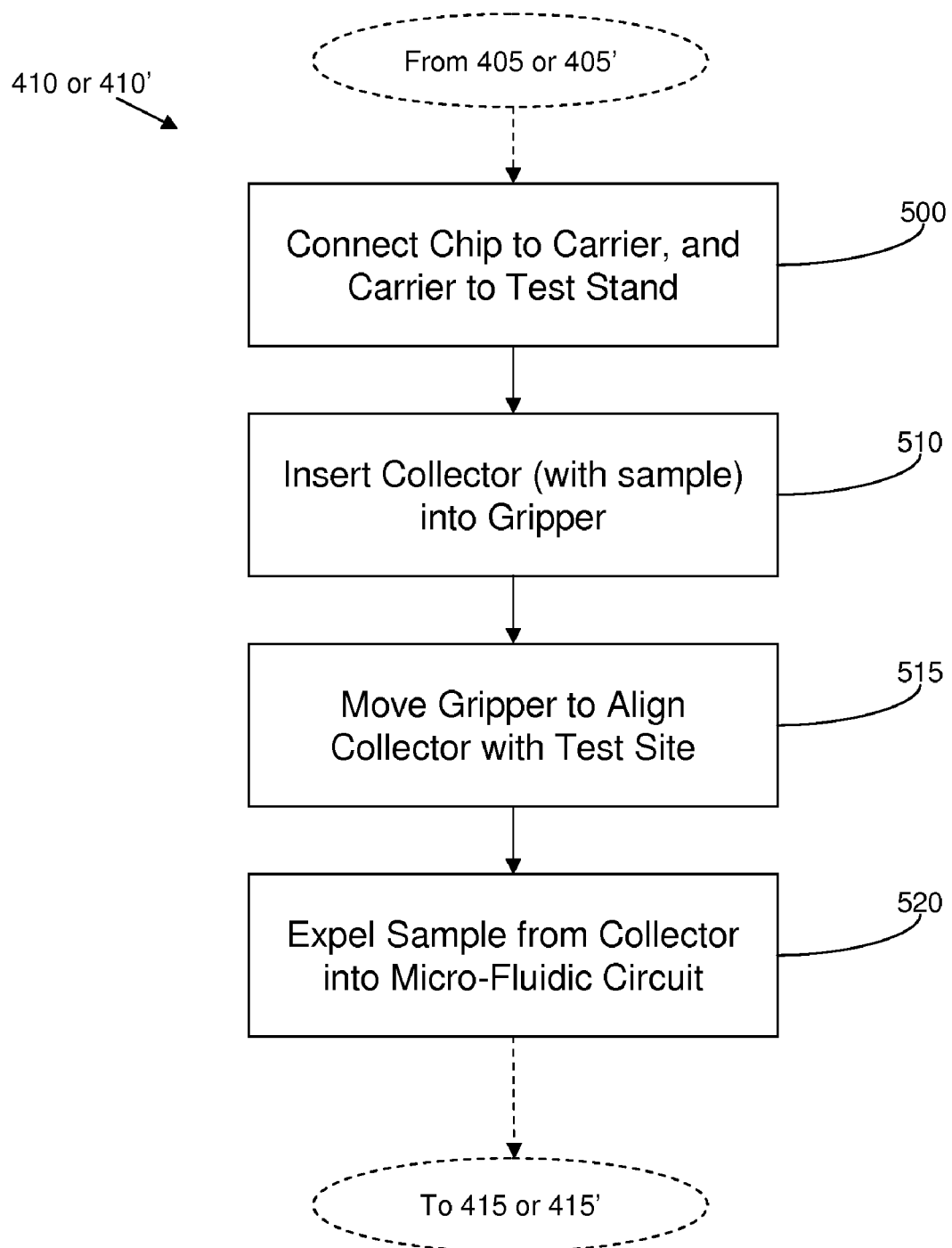

FIG. 13 shows further exemplary details of step 410 according to aspects of the invention. It is understood that FIG. 13 may also represent exemplary details of step 410'. Moreover, while FIG. 13 is described below with respect to the first system 100, it is understood that similar steps may be performed in association with the second system 200 (or any other system within the scope of the invention).

At step 500, after a fluid sample has been collected, a chip is connected to a carrier and both are connected to a test stand. In embodiments, this comprises inserting a chip into receiving portion of carrier such that the pads of the chip contact the contact portions. The carrier is then connected to the test stand via the pegs. Alternatively, the carrier may first be connected to the test stand, and then the chip connected to the carrier. In this manner, the various electrical circuits of the chip are brought into communication with the selecting device and determiner via the pads and contact portions. Moreover, as a result of step 500, the test sites of the chip are spatially located in known positions relative to the test stand such that a collector may be precisely aligned with a test site.

At step 510, the collector is inserted into the gripper. In embodiments, the combination gripper/expeller shown in FIG. 8 is used. For example, step 510 may comprise opening the gripper body, placing the collector along the seal portion such that the top of the collector extends into the gap, and closing the gripper body around collector. In this manner, the collector (and, therefore, the fluid sample held therein) is connected to the test stand such that it may be moved to and precisely aligned with a test site.

At step 515, the gripper is moved to align the collector with a respective test site. In embodiments, this comprises using the mover to move the gripper along any of three orthogonal axes. Because the test sites of the chip are spatially located in known positions relative to the test stand, the mover may be pre-programmed to automatically move the gripper such that the gripped collector is aligned with a particular test site. After alignment of the collector above a test site, the mover may further move the gripper (e.g., axially in the direction of the longitudinal axis of the collector) such that the a lower end of the collector moves through a funnel and into a position just above the large hole of the particular test site.

At step 520, the fluid sample is expelled from the collector into the micro-fluidic circuit. For example, a force (as depicted by the arrow shown in phantom lines in FIG. 8) may be applied to the membrane of the expeller. The movement of the membrane into the gap increases the air pressure behind the fluid sample in the collector, and pushes the fluid sample out of the end of the collector. As described above, the force may be applied to the membrane in any known manner (such as, for example, by piezoelectric actuator, air pump, compressed air, etc.) and the mechanism for applying the force may be integrated into the test stand.

Still referring to step 520, the fluid sample fills the large hole of the respective test site when it is expelled from the collector. The fluid flows from the large hole into the offset small hole by way of gravity and/or capillary action. The fluid continues to flow through the tunnel by way of capillary action, while the vent hole allows air that was in the tunnel to escape as the fluid fills the tunnel. At least one property of the fluid may be measured while the fluid is flowing through the micro-fluidic circuit. By keeping the fluid at least partially (and, preferably, mostly) enclosed in the tunnel, the detrimental effects of evaporation on such measurements may be minimized or avoided.

Figure 14:
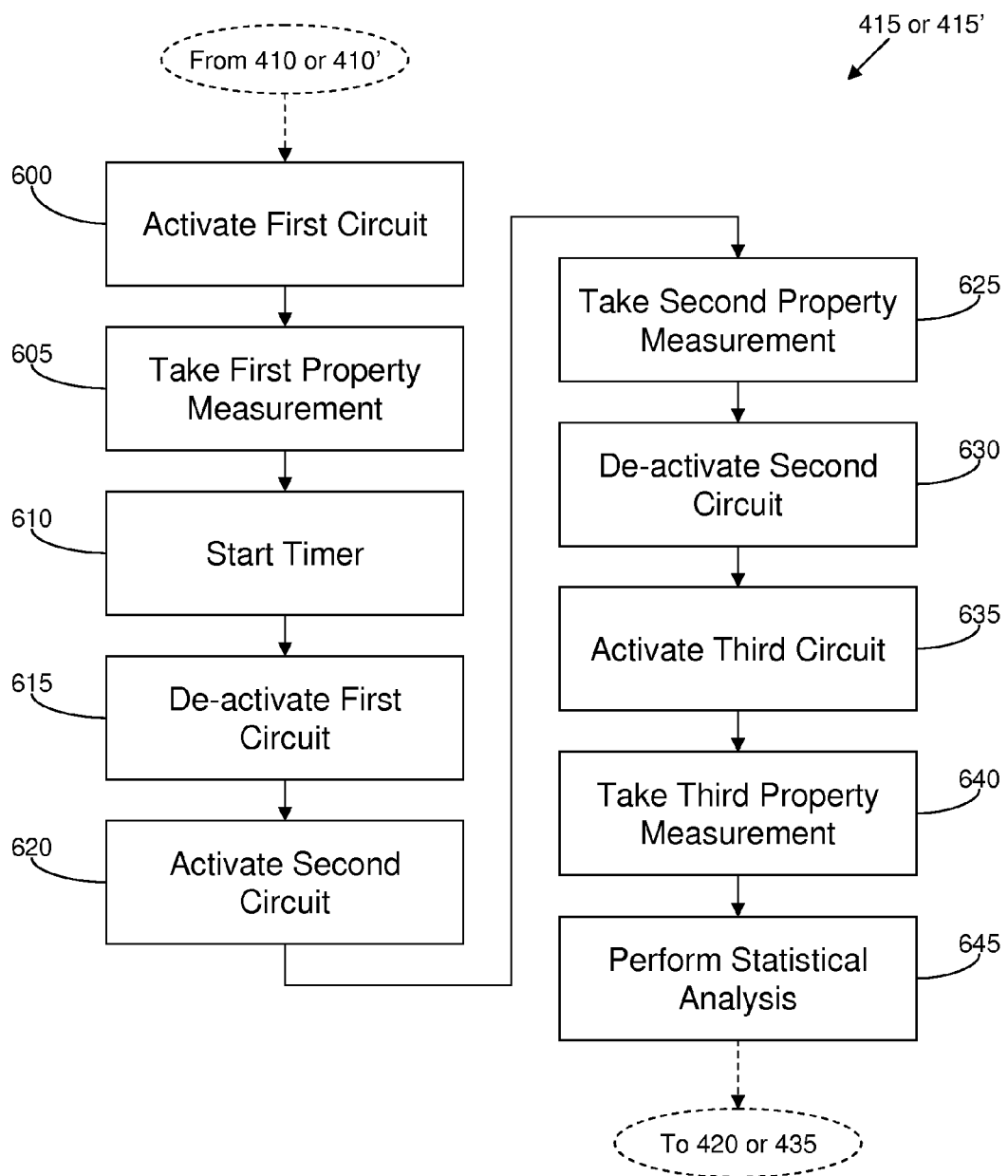

FIG. 14 shows further exemplary details of step 415 according to aspects of the invention. It is understood that FIG. 14 may also represent exemplary details of step 415'. Moreover, while FIG. 14 is described below with respect to the first system 100, it is understood that similar steps may be performed in association with the second system 200 (or any other system within the scope of the invention).

At step 600, after a fluid sample has been deposited in the micro-fluidic circuit, the first of at least one electric circuit is activated. For example, when the fluid fills the small hole, the fluid creates a first circuit A1:B1 by providing an electrically conductive connection between vias 56 and 58 (see FIG. 5). In embodiments, the selecting device is used to activate this first circuit A1:B1 by bringing the respective pads of the vias 56, 58 into electrical communication with the probes 82a, 82b of the determiner. For example, the pad associated with via 56 is brought into communication with probe 82a, and the pad associated with via 58 is brought into communication with probe 82b.

At step 605, a first of at least one property measurement of the fluid is taken. In embodiments, the determiner is used to measure the resistance of the fluid in the first circuit (e.g., between the vias 56, 58) as described above. This first property measurement may be displayed and/or stored (such as, for example, in computer memory).

In embodiments, at step 610, a timer is started when the first property measurement is taken (e.g. at step 605). For example, a timer (e.g., counter) mechanism in a microprocessor may be started, as will be understood by the skilled artisan. The timer provides a mechanism for coordinating multiple property measurements of the same fluid sample in the same micro-fluidic circuit. That is, by knowing the rate of capillary action of the fluid through the micro-fluidic circuit, the time at which the fluid reaches any point along the length of the tunnel may be pre-determined. As such, by starting the timer when the fluid closes the first electrical circuit, the timer may be used to dictate when to activate subsequent circuits along the length of the tunnel. In this manner, multiple property measurements may be taken at predetermined locations and times.

At step 615, the first circuit is de-activated. This may comprise, for example, using the selecting device to deactivate the circuit A1:B1 by taking the vias 56, 58 out of communication with the determiner. The first circuit may be de-activated at any time after the first property measurement is taken but before activating the second circuit.

At step 620, the second circuit is activated. As the fluid flows through the tunnel (e.g., in the direction of the small hole toward the vent hole), it will cross first electrode 68. At this point, the fluid creates a second circuit B2:B1 by providing an electrically conductive connection between the first electrode 68 and the via 58 (see FIG. 5). In embodiments, the selecting device is used to activate this second circuit B2:B1 by bringing the respective pads of the vias 58 and 60 (or 62) into electrical communication with the probes 82*a*, 82*b* of the determiner. For example, the pad associated with via 58 is brought into communication with probe 82*a*, and the pad associated with via 60 is brought into communication with probe 82*b*.

At step 625, a second property measurement of the fluid is taken. In embodiments, the determiner is used to measure the resistance of the fluid in the second circuit (e.g., between the vias 58, 60) as described above. This second property measurement may be displayed and/or stored (such as, for example, in computer memory). In embodiments, the second property measurement is automatically taken at a predetermined time interval after the first measurement. This may be accomplished, for example, based upon the timer value.

At step 630, the second circuit is de-activated. This may comprise, for example, using the selecting device to deactivate the circuit B2:B1 by taking the vias 58, 60 out of communication with the determiner. The second circuit may be de-activated at any time after the second property measurement is taken but before activating the third circuit.

At step 635, the third circuit is activated. As the fluid continues to flow through the tunnel, it will cross second electrode 70. At this point, the fluid creates a third circuit A2:A1 by providing an electrically conductive connection between the second electrode 70 and the via 56 (see FIG. 5). In embodiments, the selecting device is used to activate this second circuit A2:A1 by bringing the respective pads of the vias 56 and 64 (or 66) into electrical communication with the probes 82*a*, 82*b* of the determiner. For example, the pad associated with via 56 is brought into communication with probe 82*a*, and the pad associated with via 64 is brought into communication with probe 82*b*.

At step 640, a third property measurement of the fluid is taken. In embodiments, the determiner is used to measure the resistance of the fluid in the third circuit (e.g., between the vias 58, 60) as described above. This third property measurement may be displayed and/or stored (such as, for example, in computer memory).

In embodiments, steps 615-640 may be performed at respective predetermined time intervals after the first measurement is taken in step 605. The respective predetermined time intervals may be determined based upon the rate of capillary action of the fluid through the micro-fluidic circuit. The timer, started in step 610, may be monitored to recognize when a particular predetermined time interval has elapsed. In this manner, the taking of multiple property measurements may be performed automatically by a controller (e.g., processor) that monitors the timer and controls the determiner and selecting device.

Although steps 600-640 have been described with respect to three measurements and circuits, the invention may comprise any suitable number of circuits (and, therefore, measurements). Moreover, the electrical circuits (e.g., vias and electrodes) may be disposed at any suitable location along the micro-fluidic circuit.

If multiple measurements are taken, then a statistical analysis of the measured values may be performed at step 645. In embodiments, a mean value and a confidence factor are calculated for all of the gathered measurements. If the confidence factor exceeds a predetermined threshold (e.g., 90%), then the mean value is treated as valid. The mean value may be correlated to an osmolarity value and then displayed (as in steps 420 and 425) or, alternatively, displayed and then correlated to osmolarity (as in steps 435 and 440). An indication that the value is valid and/or the confidence factor may also be displayed.

In embodiments, if the confidence factor does not exceed the predetermined threshold, then the mean value is treated as invalid. An indication that the value is invalid and/or the confidence factor may be displayed. Moreover, in addition to being displayed, any of the data (e.g., gathered measurements, mean value, confidence factor, osmolarity, etc.) may be stored (e.g., in computer memory, etc.) for later use and/or may be communicated over a network (e.g., LAN, WAN, Internet, wireless network, etc.).

While the invention has been described with respect to measuring the osmolarity of human tears, the invention is not limited to such applications. The invention can be used with other fluids, such as, for example, blood, urine, sweat, plasma, semen, etc. Moreover, the invention may be used to test the osmolarity fluids from any source (e.g., drinking water), not just those of humans. Thus, while the invention has been described in terms of embodiments, those skilled in the art will recognize that the invention can be practiced with modifications and in the spirit and scope of the appended claims.

What is claimed:

1. An apparatus for measuring osmolarity of a fluid, comprising:
    a chip comprising a layered structure comprising a mixture comprising silica, alumina, and magnesia;
    at least one micro-fluidic circuit disposed in the chip and formed in at least two layers of the layered structure; and
    at least one electrical circuit disposed in communication with the at least one micro-fluidic circuit structured to measure an electrical property of a fluid contained within the at least one micro-fluidic circuit, wherein the electrical property is used in determining the osmolarity of the fluid,
    wherein the at least one micro-fluidic circuit comprises
        a first hole and a second hole in a first layer of the layered structure; and a third hole and a tunnel in a second layer of the layered structure, the at least one electrical circuit comprises a first electrode disposed in the tunnel at a first location, at least one via comprising electrically conductive material extending through a third layer of the layered structure and electrically connected to the first electrode, and a second electrode disposed in the tunnel at a second location;

further comprising a determiner comprising a correlating device that automatically correlates the measured electrical property to an osmolarity value of the fluid, wherein the at least one via comprises first and second vias at a first downstream location of the tunnel relative to the third hole, further comprising third and fourth vias at a second downstream location of the tunnel relative to the third hole and electrically connected to the second electrode, and fifth and sixth vias within a perimeter of the third hole, wherein the third via is electrically connected to the fifth via to measure the electrical property between the fifth via and the second electrode; and the second via is electrically connected to the sixth via to measure the electrical property between the sixth via and the first electrode.

2. The apparatus of claim 1, wherein the fifth and sixth vias and the first and second electrodes are structured and arranged to:

measure the electrical property of the fluid when the fluid closes a circuit between the fifth and sixth vias at a first time when the fluid in placed in the third hole;

measure the electrical property of the fluid when the fluid closes a circuit between the fifth via and the first electrode at a second time as the fluid moves through tunnel, and measure the electrical property of the fluid when the fluid closes a circuit between the sixth via and the second electrode at a third time as the fluid moves through the tunnel, wherein the first time, second time, and third time are all different times.

3. The apparatus of claim 2, wherein the first, second, and third times are predetermined times based on a rate of capillary action of the fluid through the micro-fluidic circuit.

4. The apparatus of claim 2, further comprising a selecting device that selectively activates and deactivates:

a first circuit comprising the fifth and sixth vias;

a second circuit comprising the fifth via and the first electrode; and a third circuit comprising the sixth via and the second electrode.

5. The apparatus of claim 4, wherein the selecting device:

activates the first circuit at the first time;

activates the second circuit at the second time;

activates the third circuit at the third time;

deactivates the first circuit before activating the second circuit; and deactivates the second circuit before activating the third circuit.

6. The apparatus of claim 1, further comprising at least one electrically conductive pad in a forth layer of the layered structure and electrically connected to the at least one via.

7. The apparatus of claim 6, wherein:

the at least one electrically conductive pad is larger than the at least one via;

the first layer is a top layer of the layered structure; and the fourth layer is a bottom layer of the layered structure.

8. The apparatus of claim 1, further comprising:

a first electrically conductive pad in a bottom layer of the layered structure and contacting the first via;

a second electrically conductive pad in the bottom layer of the layered structure and contacting the second via;

a third electrically conductive pad in the bottom layer of the layered structure and contacting the third via;

a fourth electrically conductive pad in the bottom layer of the layered structure and contacting the fourth via;

a fifth electrically conductive pad in the bottom layer of the layered structure and contacting the fifth via; and a sixth electrically conductive pad in the bottom layer of the layered structure and contacting the sixth via.

9. The apparatus of claim 1, wherein the fifth and sixth vias and the first and second electrodes are structured to measure the electrical property of the fluid between the fifth and sixth vias, between the fifth via and the first electrode, and between the sixth via and the second electrode.

10. The apparatus of claim 1, wherein the electrical property is one of resistance and conductivity.

11. The apparatus of claim 1, wherein the determiner comprises:

first and second electrically conductive probes configured to be electrically connected to portions of the chip;

a measuring device and a current generator connected to the first and second electrically conductive probes; and a display that visually displays one of: a numerical value that corresponds to the measured electrical property of the fluid, and the correlated osmolarity value of the fluid.

12. The apparatus of claim 1, wherein:

the first layer is above the second layer; and the second layer is above the third layer.

13. The apparatus of claim 1, wherein:

the first hole overlaps and is offset from the third hole in top view;

the tunnel extends between the third hole and the second hole;

a diameter of the first hole is larger than a diameter of the third hole;

the diameter of the third hole is larger than a width of the tunnel in top view; and the chip is structured such that the fluid that is deposited in the first hole flows into the third hole by way of gravity, and the fluid flows from the third hole, into the tunnel, and toward the second hole by capillary action.

14. The apparatus of claim 1, wherein the first electrode and the second electrode each completely traverse the tunnel.

15. The apparatus of claim 1, wherein:

the first and third holes are circular in top view;

the third hole is contained within a perimeter of the first hole and offset from a center of the first hole in top view.

* * * * *